US008445278B2

(12) United States Patent
Everaerts et al.

(10) Patent No.: US 8,445,278 B2
(45) Date of Patent: May 21, 2013

(54) PROCESS FOR PRODUCING DECELLULARIZED BIOLOGICAL TISSUES

(75) Inventors: Frank J. L. Everaerts, Maastricht (NL); Mark W. Torrianni, San Juan Capistrano, CA (US); Frans M. Everaerts, Weert (NL); Paul V. Trescony, Champlin, MN (US); Wilfred den Hartog, Den Bosch (NL)

(73) Assignee: Medtronic, Inc., Minneapolis, MN (US)

( * ) Notice: Subject to any disclaimer, the term of this patent is extended or adjusted under 35 U.S.C. 154(b) by 1296 days.

(21) Appl. No.: 11/365,401

(22) Filed: Mar. 1, 2006

(65) Prior Publication Data

US 2007/0020248 A1 Jan. 25, 2007

Related U.S. Application Data

(60) Provisional application No. 60/657,764, filed on Mar. 1, 2005.

(51) Int. Cl.
*C12N 5/00* (2006.01)

(52) U.S. Cl.
USPC .......................................................... 435/378

(58) Field of Classification Search ........................ None
See application file for complete search history.

(56) References Cited

U.S. PATENT DOCUMENTS

| | | | |
|---|---|---|---|
| 4,553,974 A | 11/1985 | Dewanjee | |
| 4,801,299 A | 1/1989 | Brendel et al. | |
| 6,166,184 A | 12/2000 | Hendriks et al. | |
| 6,177,514 B1 | 1/2001 | Pathak et al. | |
| 6,322,593 B1 | 11/2001 | Pathak et al. | |
| 6,409,774 B1 * | 6/2002 | Kerschmann et al. | 8/444 |
| 6,509,145 B1 | 1/2003 | Torrianni | |
| 2002/0115208 A1 | 8/2002 | Mitchell et al. | |
| 2003/0087428 A1 * | 5/2003 | Wolfinbarger et al. | 435/325 |
| 2005/0020506 A1 | 1/2005 | Drapeau et al. | |
| 2005/0119736 A1 | 6/2005 | Zilla et al. | |
| 2005/0266390 A1 | 12/2005 | Ueda et al. | |

FOREIGN PATENT DOCUMENTS

| | | |
|---|---|---|
| WO | 95/24873 | 9/1995 |
| WO | 02/072165 | 9/2002 |
| WO | 02/072165 A1 | 9/2002 |

OTHER PUBLICATIONS

Xia, et al., BD Biosciences Discovery Labware, Becton Dickinson and Company, Woburn, MA, S03T120 (2003).
Kasimir, et al., "Comparison of different decellularization procedures of procine heart valves," The International Journal of Artificial Organs, vol. 26, No. 5, (2003), pp. 421-427.
Rieder, et al., "Decellularization protocols of porcine heart valves differ importantly in efficiency of cell removal and susceptibility of the matrix to recellularization with human vascular cells," J. Thor. Cardiovasc. Surg., vol. 127, No. 2, (2004) pp. 399-405.
Wilson, et al., "Acellular Matrix: A Biomaterials Approach for Coronary Artery Bypass and Heart Valve Replacement," Ann. Thorac. Surg., 1995;60-S353-8.
Non-final Office Action from U.S. Appl. No. 10/858,174, mailed Dec. 29, 2005 (19 pages).
Final Office Action from U.S. Appl. No. 10/858,174, mailed Jul. 26, 2006 (14 pages).
International search report from International Patent Application No. PCT/US2005/018578 (7 pages).
Jones, et al., "The Effects of Anticalcification Treatments on Bioporsthetic Heart Valves Implanted in Sheep" Trans. Am. Soc. Artif. Intern. Organs, 34:1027-1030 (1988).
Jones, et al., "Anticalcification Treatments of Bioprosthetic Heart Valves: In Vivo Studies in Sheep," Journal of Cardiac Surgery 4:69-73 (1989).

* cited by examiner

*Primary Examiner* — Allison Ford

(57) ABSTRACT

The present invention provides an electrophoretic system, apparatus, and method of use thereof for the preparation of a tissue-derived bioprosthesis.

19 Claims, 3 Drawing Sheets

PROCESS FOR PRODUCING DECELLULARIZED BIOLOGICAL TISSUES

CROSS-REFERENCE TO RELATED APPLICATIONS

This application claims priority from U.S. provisional application Ser. No. 60/657,764, filed Mar. 1, 2005, the entire contents of which are incorporated by reference herein.

BACKGROUND OF THE INVENTION

Over 250,000 patients a year worldwide undergo heart valve replacement. In general, there are two possible choices for replacement heart valves, viz., mechanical or biological prostheses. Biological heart valve prostheses have many advantages over mechanical devices.

Autologous tissue from fresh or cadaveric sources, i.e., human tissue, can be used in the production of biological prostheses (bioprostheses) for human implantation. The shortage of autologous donor material, which presents a supply problem, can be overcome by using alternative sources for tissue, such as animal tissue. To prevent the immunological rejection of animal tissue-derived bioprostheses once they are implanted into a human recipient, animal tissue can be treated using processes such as disclosed in U.S. Pat. Nos. 6,166,184 and 6,509,145; and published U.S. Patent Application Nos. 20030118981A1, 20050020506A1 and 20050266390A1.

Despite their many advantages, a major drawback to the use of biological heart valve prostheses is their relative poor durability as compared to the durability of mechanical devices. To enhance the durability of bioprostheses, tissue engineering efforts have been made to produce tissue "scaffolds" that can be regenerated, i.e., recellularized, with host cells once implanted in a recipient.

However, there is still a need in the art for durable, non-immunogenic and viable bioprostheses that are amenable to healing and to growth, for example, in children, as well as a process for preparing such bioprostheses. In addition, there is a need for a process for decellularizing harvested biological (e.g., animal) tissue and extracting antigens from the tissue in order to provide bioprostheses suitable for human use, thus offering a viable alternative to allogeneic donor tissue.

SUMMARY

A process has been invented to enhance the durability of tissue-derived bioprostheses such as bioprosthetic heart valves, e.g., stentless porcine aortic heart valve substitutes. In one embodiment of this process, tissue is decellularized with the ionic detergent sodium dodecyl sulphate (SDS). Because SDS is difficult to remove from the tissue after decellularization, the present invention provides an improved rinse procedure.

The methods of the present invention are related to a detergent-based treatment method (decellularization method) that is described in U.S. Patent Application publication No. 20050266390A1. The methods of U.S. Patent Application publication No. 20050266390A1 and of the present invention strike a balance between xeno-antigen extraction and extracellular matrix preservation. The methods of the present invention can be applied to a broad variety of tissues, and could serve as a platform technology for many implantable products. The present invention provides methods to accelerate antigen extraction from tissue in the preparation of tissue-derived, implantable bioprostheses.

The present invention provides a method for preparing a tissue-derived bioprosthesis comprising subjecting tissue to an electrophoretic field to extract at least one electrically charged substance from the tissue to provide a tissue-derived bioprosthesis. In certain embodiments of the method, the electrically charged substance comprises a decellularization agent, a cellular component of the tissue, or any combination thereof. One embodiment of the method further comprises contacting the tissue with a decellularization solution for up to about 170 hours, for example, up to about 50 hours. In certain aspects of the invention, the cellular component comprises a cell membrane protein, an intracellular protein, a non-structural extracellular matrix protein, a nucleic acid, a glycoprotein, a fragment thereof, a portion thereof, a derivative thereof or any combination thereof. In one embodiment of the invention, the tissue is mammalian tissue, for example, aortic tissue, pericardial tissue, venous tissue, arterial tissue, a component thereof or any combination thereof. In one aspect of the invention, the aortic tissue component comprises collagen, elastin, hyaluronic acid, or any combination thereof. The mammalian tissue can be, for example, human, porcine, bovine, marsupial, ovine, or canine tissue. In one embodiment, the mammalian tissue is porcine tissue. In another embodiment, the mammalian tissue is bovine tissue. In certain aspects of the invention, the tissue comprises fresh tissue, cadaveric tissue, fixed tissue or unfixed tissue. In one embodiment of the method, the decellularizing agent comprises a negatively charged molecule, including an ionic detergent such as an anionic detergent, e.g., sodium dodecyl sulphate or a derivative thereof. In certain embodiments of the method, the bioprosthesis is substantially free of SDS, e.g., comprises up to about 0.5 g/L SDS or up to about 0.006% SDS. One aspect of the invention provides for an electrophoretic field applied perpendicularly to the tissue. In one embodiment, the tissue is subjected to the electrophoretic field for less than 600 hours, for example, about 200 hours. In one embodiment, the electrophoretic field is applied in the range of about 1 mA to about 15 mA. In yet another embodiment, an electrophoretic field has an applied potential of about 2V to about 20V. Certain aspects of the method further comprise washing the tissue to remove tissue debris, blood, fluid, fat, or any combination thereof prior to subjecting the tissue to the electrophoretic field. Certain aspects of the invention further comprise rinsing the tissue with a rinse solution. In one embodiment, the tissue is rinsed with an inflow velocity of about 0.5 L/min. In another embodiment, the tissue is rinsed with an inflow velocity of about 0.33 mm/s to about 6.6 mm/s, e.g., about 1.67 mm/s to about 6.6 mm/s. Certain aspects of the invention further comprise subjecting the tissue to pulsatile flow.

The invention also provides a method for preparing a tissue-derived bioprosthesis comprising contacting tissue with at least one electrically charged substance and subjecting the tissue an electrophoretic field so as to cause the electrically charged substance to be electrophoretically transported into and/or out of the tissue to provide the tissue-derived bioprosthesis. In certain embodiments of the method, the electrically charged substance comprises a fixative agent, a decellularization agent, a recellularization agent, a bioactive agent, or any combination thereof. For example, the contacting is simultaneous, separate or sequential. In one embodiment, the electrically charged substance is electrophoretically transported into the tissue. In another embodiment, the electrically charged substance is electrophoretically transported out of the tissue. In certain embodiments of the method, the tissue comprises an electrically charged macromolecule comprising native tissue protein, nucleic acid, a portion thereof, a fragment thereof or a derivative thereof. In one embodiment, the electrically charged macromolecule is electrophoretically transported out of the tissue. In another aspect of the method, the electrically charged substance is a decellularization agent. In one embodiment, the agent complexes with a native tissue protein, nucleic acid, a portion thereof, a fragment thereof or a derivative thereof. In one aspect of this method, the complex is electrophoretically transported out of the tissue. In another embodiment of the method, the fixative agent comprises gluteraldehyde or a derivative thereof. In yet another embodiment, the recellularization agent comprises a chemoattractant, a growth factor, a cytokine, a chemokine, or any combination thereof.

In addition, the present invention provides a tissue-derived bioprosthesis comprising decellularized tissue that is substantially free of decellularization agents, substantially free of antigens, wherein the bioprosthesis is readily recellularized in vivo when implanted into an intended recipient. In certain embodiments, the tissue-derived bioprosthesis is non-immunogenic to the intended recipient. In other embodiments, the tissue-derived bioprosthesis is non-inflammatory to the intended recipient. In one embodiment, the tissue-derived bioprosthesis is a heart valve. In one embodiment, the decellularized tissue comprises extracellular matrix structural proteins, such as collagen and elastin. In certain embodiments, the tissue is xenogeneic to an intended recipient. In other embodiments, the tissue is allogeneic to an intended recipient.

Additionally, the invention provides a system for the electrophoretic treatment of tissue, the system comprising an electrophoretic apparatus comprising housing, a first electrolyte chamber containing a first electrode, for example, an annular electrode; a second electrolyte chamber containing a second electrode, for example, a cylindrical electrode, wherein the second electrolyte chamber is disposed relative to the first electrolyte chamber so that the electrodes are adapted to generate an electric field in an electric field area upon application of an electric potential between the electrodes; a sample chamber disposed between the first and second electrolyte chambers and at least partially disposed in the electric field area; a first electrolyte reservoir and a second electrolyte reservoir in fluid communication with the first and second electrolyte chambers, respectively; a power supply; a pump; a flow meter; a filter; and a buffer reservoir. In one embodiment, the system further comprises an ion exchange column.

DETAILED DESCRIPTION OF THE INVENTION

I. Definitions

Figure 1:
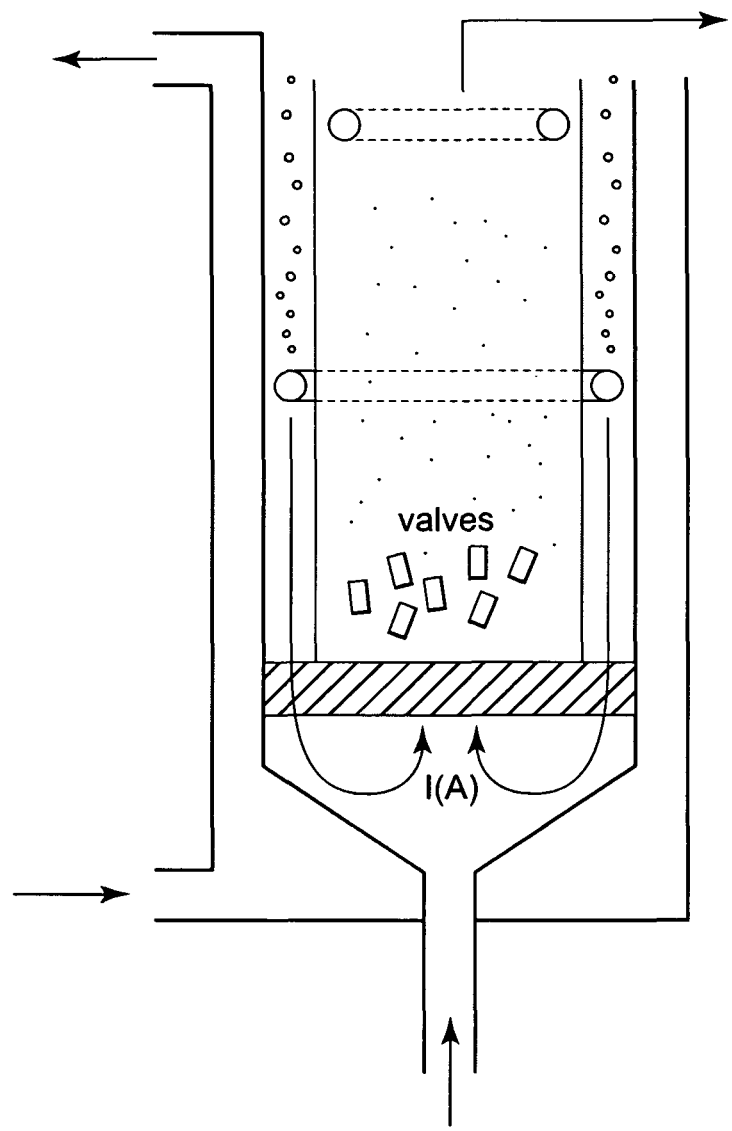
FIG. 1 shows a process for removal of components from tissue valves using gravity, mechanical flow and electrophoretic created flow.
Figure 2:
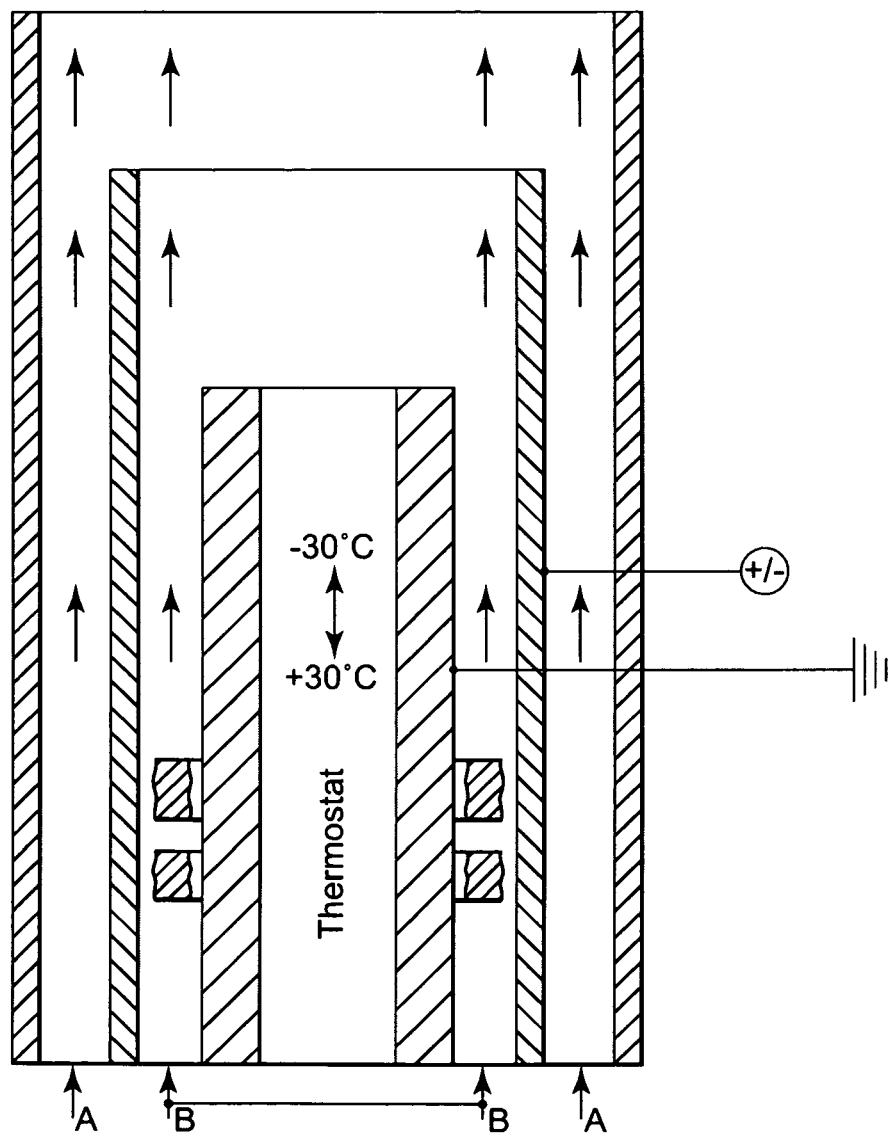
FIG. 2 shows electrophoretic adsorption and ion-exchange.

Unless otherwise specified, "a," "an," "the," and "at least one" are used interchangeably herein and mean one or more than one.

With respect to a recipient, an "allogeneic" cell or "allogeneic" tissue originates from or is derived from a donor of the same species as the recipient. A "xenogenic" cell or tissue originates from or is derived from a donor of a different species than the recipient. A "xenograft" or "heterograft" is a graft transferred from an animal of one species to one of another species. Also with respect to the recipient, an "autologous" cell or "autologous" tissue originates with or is derived from the recipient. An "allograft" or "homograft" is a graft transplanted between genetically nonidentical individuals of the same species. An "autograft" is a graft transplanted from one site to another within an individual.

As used herein, the term "mammal" includes any mammalian species, including primate, such as human, as well as porcine, bovine, ovine sheep, equine, and the like.

The term "decellularization" refers to the removal and/or extraction of cells and/or cellular components from a tissue. Using methods of the invention, cellular components are removed from tissue by decellularization without damaging the structure and/or function of the tissue. Moreover, non-cellular components are retained in the tissue following decellularization using the methods of the invention. Therefore, a "decellularization agent" refers to a substance capable of decellularizing a tissue.

The phrase "cellular component," as used herein, refers to substances that constitute a portion of a cell, including cell membranes and macromolecules (e.g., nucleic acids, polypeptides, glycoproteins, etc.) that are normally found enclosed within a cell membrane, embedded within a cell membrane, or attached to a cell membrane. The term does not include molecules that have been secreted by cells, e.g., extracellular matrix components such as collagen, elastin, proteoglycans, etc., even if such molecules are associated with or linked to the cell surface.

The term "nucleic acid" refers to deoxyribonucleotides or ribonucleotides and polymers thereof in either single- or double-stranded form, composed of monomers (nucleotides) containing a sugar, phosphate and a base which is either a purine or pyrimidine. Deoxyribonucleic acid (DNA) in the majority of organisms is the genetic material while ribonucleic acid (RNA) is involved in the transfer of information contained within DNA into proteins. The terms "nucleic acid," "nucleic acid molecule," "nucleic acid fragment," "nucleic acid sequence or segment," or "polynucleotide" may also be used interchangeably with gene, cDNA, DNA and RNA encoded by a gene.

The terms "polypeptide," "protein," and "peptide" are used interchangeably herein. It is well-known in the art of protein biochemistry that amino acids, the 'building blocks' of proteins, have particular sizes and characteristics, such as charge, hydrophobicity and hydrophilicity. For example, nonpolar (hydrophobic) amino acids include alanine, leucine, isoleucine, valine, proline, phenylalanine, tryptophan, and tyrosine. Polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid.

By "fragment" or "portion" is meant a full length or less than full length of the nucleotide sequence encoding, or the amino acid sequence of, a polypeptide or protein.

By "non-cellular component" is meant a substance present within a biological tissue (either a native tissue or a tissue-engineered construct) that was derived from a cell or was present within the tissue but is not contained within the plasma membrane of a cell. Examples of such components include extracellular matrix (ECM) components (e.g., elastin, collagen (Type I, IV), laminin, fibronectin, etc.) and the like.

"Native" refers to naturally occurring. Thus, by "native tissue protein," for example, is meant a protein that is present in naturally occurring tissue, i.e., tissue from a mammal that remains substantially intact and substantially retains the structure naturally found within the body of the mammal.

The terms "antigen" and "immunogen" are used interchangeably herein, and refer to any substance that elicits an immune response when administered to a mammal.

As used herein, the term "recellularization" refers to the colonization or re-population of a bioprosthesis with recipient cells following implant, for example, the replacement of cells that originally existed in tissue prior to decellularization with host cells, e.g., infiltrating cells. Thus, a "recellularization agent" is a substance that promotes, induces or enhances the recellularization and/or the revitalization of a bioprosthesis of the invention.

Recellularization agents include, but are not limited to, bioactive molecules attract precursor cells to the bioprosthesis, e.g., bioactive molecules capable of attracting fibroblast and/or endothelial cells and/or precursors thereof. Exemplary recellularization agents include, but are not limited to, chemoattractants, growth factors, cytokines, chemokines and derivatives thereof. A "cytokine" is a physiologically active substance that is produced by a cell and acts on the same or different cell. Cytokines are generally proteins or polypeptides, which have an action of controlling an immune response, an action of regulating an endocrine system, an action of regulating a nerve system, an anti-tumor action, an anti-virus action, an action of regulating proliferation, an action of regulating differentiation, and the like. As used herein, cytokines may be in the form of proteins or nucleic acids, or in other forms. By "growth factor" is meant a substance capable of promoting or controlling cell growth. Growth factors are also referred to as proliferation factors or development factors.

By "cytotoxic" is meant having a detrimental or destructive affect on cells.

By "substantially-free" means that the presence of a particular agent is either not detected using any known assays or any assay described herein, or if it is detected, it is present at a concentration or amount that is insubstantial, i.e., so little agent so as to not affect downstream features, such as durability or viability, of a tissue-derived bioprosthesis of the invention. For example, by "substantially-free" of SDS ("SDS-free") is meant having a concentration of SDS below that which is cytotoxic. For example, SDS is toxic to fresh rat hepatocytes at concentrations of about 0.01 mM or more ($IC_{50}$=0.049 mM) (Xia et al., BD Biosciences Discovery Labware, Becton Dickinson and Company, Woburn, Mass., S03T120 (2003); at concentrations of up to about 0.006% by weight, and at concentrations up to about 0.5 g/L. Thus, a tissue-derived bioprosthesis is "substantially free of SDS" or "SDS-free" when SDS is present in the bioprosthesis at less than toxic amounts.

"Bioactive agent" refers to an agent that exerts a physiologic effect, e.g., a therapeutic effect on biological tissue. As used herein, the term "therapeutic agent" refers to any agent or material that has a beneficial effect on the mammalian recipient. Thus, "therapeutic agent" embraces both therapeutic and prophylactic molecules having nucleic acid or protein components.

As used herein, the phrase "effective amount" refers to an amount that causes a detectable biological change in a target cell population, and preferably an amount that accomplishes a therapeutic effect, i.e., reduces at least one symptom of a pathology or disease afflicting a mammal, or a prophylactic effect.

The words "comprise," "comprising," "include," "including," and "includes" when used in this specification are intended to specify the presence of stated features, integers, components, or steps, but they do not preclude the presence or addition of one or more other features, integers, components, steps, or groups thereof.

II. The Tissue-Derived Bioprostheses of the Invention

A. Properties

In the preparation of tissue-derived bioprostheses, tissue, e.g., xenogenic tissue, is treated to minimize the immunogenicity of the implant to the recipient. For example, tissue is decellularized to remove tissue cells and proteins, e.g., cell membrane glycoproteins, from the extracellular matrix (ECM) of the tissue cell. Methods for treating tissue, including decellularization procedures, are known to the art. For example, U.S. patent application Publication No. 20050266390 discloses contacting a tissue sample with a decellularization solution having 0.5% SDS and 0.5% Triton X-100 for 1 week. The present inventors found that this method was "gentle" to the extracellular matrix of decellularized tissue samples. In particular, it was found that the collagen structure of the ECM of the tissue remained unaffected, as shown by histology, electron microscopy and calorimetry (data not shown). The present inventors subjected porcine aortic valves that were decellularized using these methods to up to 200 million cycles of in vitro accelerated wear testing. A gradual loss of glycosaminoglycans (GAGs) from the ECM was observed, but no substantial structural deterioration of the tissue was found. Moreover, as shown by the abolishment of immunostaining with serum from rabbits immunized against fresh pig valve extracts, porcine antigens were effectively removed from the valve (data not shown). These data were consistent with the finding that subdermal implants in rats and monkeys and pulmonic valve replacements in dogs elicited minimal inflammation (data not shown).

However, the present inventors discovered that spontaneous in vivo recellularization of implants with non-inflammatory cells prepared using the process was slow. It was discovered that the presence of residual SDS in the decellularized tissue was cytotoxic at concentrations of above 0.006%.

The present invention provides a tissue-derived bioprosthesis that is substantially free of decellularization agents such as SDS, substantially free of antigens or immunogens, and optionally supplemented with bioactive agents and/or recellularization agents such as chemoattractants to promote recellularization of the bioprosthesis with recipient or host cells after the bioprosthesis is implanted. In accordance with the other aspects of the invention, which provide methods, system and apparatus for preparing such a bioprosthesis, residual SDS, i.e., SDS that is present in decellularized tissue following a decellularization process, is removed from the decellularized tissue. In addition to its inflammatory properties, such SDS may be associated with antigens or immunogens present in the tissue, such as cellular proteins, for example, non-structural proteins of the ECM, glycoproteins, etc. Thus, the tissue-derived bioprosthesis of the present invention can be implanted into an intended recipient with reduced immunogenic and/or inflammatory response(s).

In one embodiment of the invention, a tissue-derived, implantable bioprosthesis is provided that approximates a native mammalian heart valve, for example, the bioprosthesis has mechanical, functional, structural and/or physiological properties similar to that of a native mammalian heart valve. For example, in one embodiment, the invention provides an implantable, tissue-derived heart valve bioprosthesis having the durability properties of a native heart valve. Values for the mechanical, functional, structural and physiological properties of native heart valves are known and can be calculated using methods known in the art.

B. Sources of Tissue

The tissue-derived implantable bioprosthesis of the present invention may be prepared using the tissue of any mammalian species, for example, primate (including human), porcine, bovine, ovine, equine, canine, marsupial (e.g., kangaroo), and the like, as a tissue source. The tissue may be obtained from a cadaveric source. The present invention can also utilize tissue obtained through cell culture as a tissue source for the bioprosthesis, e.g., an in vitro produced tissue construct.

Examples of types of tissue useful to prepare the tissue-derived implantable medical devices of the invention include, but are not limited to, porcine aortic root tissue, bovine aortic root tissue, facia, omentum, porcine and/or bovine pericardium or veins and arteries, including carotid veins and arteries. In one embodiment, porcine aortic root is used as a tissue source. In another embodiment, bovine pericardial tissue is used as a tissue source.

The tissue-derived implantable bioprostheses of the invention tissue may be used as implants, tissue fillers, burn dressings, wound dressings, and other applications well known to those skilled in the art. For instance, blood vessels, such as mammalian, e.g., porcine or bovine, veins or arteries may be cleansed of native (naturally occurring) protein(s) and used for blood vessel grafts or replacements in humans.

III. Harvesting and Initial Treatment of Tissue

Tissue is harvested from its source using techniques known to the art. For example, standard biopsy techniques may be employed. In one embodiment, tissue is obtained directly from a slaughterhouse and is dissected to remove undesired surrounding tissue. Either immediately following harvest or shortly thereafter, but prior to significant tissue damage and/or degradation, the tissue can be treated according to methods of the present invention. In one method, once the tissue is obtained, it is shipped on ice in order to reduce autolytic damage to the tissue and to minimize bacterial growth during shipment. In some methods, the tissue is shipped and received within about 24 hours to a location where treatment of the tissue, as described herein, can be performed. In another embodiment, tissue is cultured in vitro, e.g., using tissue culture techniques known to the art, and harvested. Once harvested, tissue can be treated by the various steps of the invention in any of a wide variety of orders.

In one embodiment of the invention, the tissue is placed in a wash solution following harvest to removes extraneous tissue debris, blood components, culture medium, etc., using techniques known to the art. For example, the tissue can be washed with a non-phosphate buffered organic saline solution or a chelating, non-phosphate saline (NPS) solution as described in U.S. Pat. No. 6,509,145 and U.S. Patent application 20050266390, respectively. The wash solution may stabilize the tissue's extracellular matrix while assisting in the removal of excess blood and body fluids that may come in contact with the tissue. The wash solution for use in the present invention can contain, for example, a saline solution having about 0.1% to 1.0% NaCl by weight. A chelating agent may be present in the wash solution at a concentration of about 10 mM to about 30 mM. Suitable chelating agents include, for example, EDTA (ethylenediaminetetraacetic acid), EGTA (ethylenebis(oxyethylenenitr-ilo) teteraacetic acid), citric acid, or salts thereof, and sodium citrate. The wash solution may also include an antibacterial compound, for example, sodium azide. In addition, the wash solution may contain protease inhibitors, for example, AEBSF (Available from Sigma as P2714), E-64, B-statin, leupeptin, and/or aprotinin. The pH of the wash solution depends upon the type of tissue, nature of antigens present and type of decellularization agent(s) that are used, for example, in the range of about pH 6 to about pH 8, e.g., about pH 7.4.

During the wash procedure the tissue can be subjected to mechanical processing by any number of methods. For example, a roller bottle apparatus can be employed to keep the treated tissue suspended during treatment. Employing a tissue roller bottle apparatus may be advantageous in that it may further assist in the diffusion of materials from the tissue by maintaining the concentration gradient between materials to be extracted from the tissue and the concentration of the material in the volume of the extraction solution. The temperature during the wash treatment can be maintained at about room temperature, for example, between about 20° C. and 30° C.

In one embodiment, the tissue is placed into a decellularization solution within two hours, one hour, or even a half-hour from the time of harvest. Thus, the decellularization step can begin immediately after harvest before tissue can begin autolytic degradation. When such immediate contact with decellularization solution is performed, the wash step may be performed after the tissue is received at the tissue treatment site, followed by further contact with decellularization solution, or the decellularization solution can be changed with fresh decellularization solution, and the wash step effectively skipped.

IV. Subsequent Treatment of the Tissue

A. Decellularization

Decellularization protocols are known in the art and may be accomplished using any of a variety of detergents, emulsification agents, proteases, and/or high or low ionic strength solutions. See, for example, U.S. patent application Publication No. 20050266390.

In certain embodiments of the invention, decellularization is performed under conditions and for sufficient times such that antigens, e.g., immunogenic cellular components including lipid membranes, membrane associated antigens and soluble proteins present in the tissue sample, are substantially removed, while the structural and mechanical integrity of the cell, the cell's ECM and the ECM proteins, e.g. collagen and elastin, are maintained. In particular, the decellularization solution facilitates the breakdown of the cellular structure in the tissue sample for the removal of cells, as well as cell debris and cell organelles from the ECM, and proteins, by breaking up the phospholipid bilayer of cell membranes. The decellularization solution contains at least one decellularization agent that is capable of associating, e.g., attaching permanently or temporarily via a covalent bond, ionic bond, hydrogen bond or van der Waals forces, so as to form a complex with macromolecules, e.g., proteins, including immunogenic or antigenic proteins, and/or nucleic acids, that are present on or within the cell and/or cell membranes. The decellularization solution of the invention does not cause gross alteration in the structure of the tissue sample, the ECM of the tissue sample, or in its biomechanical properties. The effects of decellularization on structure may be evaluated by known techniques, including light microscopy, ultrastructural examination, histology, electron microscopy, calorimetry, etc. In addition, biomechanical tests, which are well known in the art, may be used to evaluate the effects of various decellularization protocols on tissue properties. Selection and interpretation of such tests will depend, in general, upon the nature of the construct and the purpose for which it is intended.

The concentration of the decellularization agent used to decellularize the tissue varies depending on the desired requirements. The total concentration of decellularization agent added to the solution can be about 0.01% to about 10% by weight. The total concentration of all decellularization agents added to the decellularization solution can be about 2 weight percent or less in some embodiments. The total concentration of decellularization agent(s) in some methods is between about 0.25 percent and about 2 percent (weight by volume or volume by volume), for example, between about 0.5 percent and about 1 percent.

In addition, the decellularization solution can also contain between about 0.1% and 1% saline by weight and between about 0.025% and 0.1% by weight sodium azide.

The tissue can be placed in the decellularization solution for periods of up to about 7 days. In other embodiments, the tissue is placed in the decellularization solution for about 70 hours, about 60 hours, about 50 hours or about 40 hours or less, depending on the embodiment and depending on the tissue thickness, and/or tissue density. The tissue-contacting period can be long enough to allow non-structural proteins and/or antigens associating, e.g., forming protein-detergent complexes, present in the tissue with the detergent. In one method, the tissue is placed in contact with the decellularization solution for at least about 40 hours. In another method, tissue about 2 mm thick is placed in contact with the decellularization solution for about 50 hours. Tissue constructs from tissue culture may require only about 2 days or less depending on the construct. Denser tissue may require longer contact times. For example, femoral artery tissue may require a longer contact time than femoral vein tissue.

As with during the wash procedure, the tissue can be subjected to mechanical processing during decellularization by any number of methods. For example, a roller bottle apparatus can be employed to keep the treated tissue suspended during treatment.

The tissue and decellularization solution can be maintained at a temperature of between about 20 to 40° C.

In one embodiment of the invention, the tissue is contacted with the decellularization solution after the washing step.

Decellularized tissue can then be rinsed using standard protocols or by methods described hereinbelow to substantially remove the decellularization agent from the tissue thickness center.

In certain embodiments of the present invention, assays are conducted to determine the presence or absence of macromolecules, e.g., nucleic acid molecules and/or protein molecules, in the tissue following decellularization. A variety of assays may be performed, including, for example, "molecular biological" assays well known to those of skill in the art, such as Southern and Northern blotting, RT-PCR and PCR; and "biochemical" assays, such as detecting the presence or absence of a particular protein, e.g., by immunological means (ELISAs and Western blots). See, for example, Sambrook and Russell, *Molecular Cloning: A Laboratory Manual*, $3^{rd}$ Edition, Cold Spring Harbor Laboratory Press, Cold Spring Harbor, N.Y. (2001); Mullis et al., *Cold Spring Harbor Symp. Quant. Biol.*, 51, 263 (1987); Erlich, ed., *PCR Technology*, (Stockton Press, N.Y., 1989). In certain embodiments of the invention, polymerase chain reaction (PCR) is performed to verify that decellularized tissue is free of host nucleic acids, e.g., free of porcine retrovirus DNA.

Following the decellularization process, the decellularized tissue preparation is further processed using methods of the present invention to order to remove the decellularization solution as well as any residual antigenic proteins, e.g., the detergent-protein complexes, from the tissue sample.

B. Electrophoretic Treatment

As discussed above, a xenograft can provoke immunogenic reactions such as chronic and hyperacute rejection of the xenograft once implanted into a recipient. Even tissue-derived bioprostheses prepared from tissue that is allogenic to an intended recipient can be immunogenic. Methods to reduce the inflammatory and immunogenic responses caused by xenogenic and allogenic tissue are known, for example, tissue can be chemically treated, such as by gluteraldehyde, and/or decellularized by methods known to the art. However, because macromolecules diffuse out of decellularized tissue slowly, immunologic or inflammatory reactions may still be induced upon implanting a bioprostheses prepared from decellularized tissue.

The present invention provides a method to remove, extract and/or elute residual cells and/or macromolecules such as nucleic acids, proteins and/or decellularization agents by driving the macromolecules out of tissue under the influence of an electric field. In one embodiment of the method of the invention, a tissue-derived bioprosthesis is made by contacting tissue with a decellularization solution that contains at least one decellularization agent. The decellularization agent is either an agent that is charged or is capable of being charged, and in addition is capable of associating so as to form a complex with a macromolecule, e.g., a protein, nucleic acid, etc. that is present in the tissue sample. The protein and/or nucleic acid may be antigenic or immunogenic. In certain embodiments of the invention, the decellularization agent is an ionic detergent, e.g., an anionic detergent such as sodium dodecyl sulphate (SDS), sodium sodecyl sulfonate, sodium dodecyl sarcosinate, and derivatives thereof.

In one embodiment of the invention, the decellularization agent is sodium dodecyl sulphate (SDS). As discussed herein, most proteins carry a net negative charge at neutral pH. SDS solubilizes, denatures and binds to proteins, and in so doing confers a supplemental negative charge to a particular protein in proportion to its length. SDS-polyacrylamide gel electrophoresis (SDS-PAGE) is a well-known technique in which protein-SDS complexes are 'driven' through a gel via an electric field. In one embodiment of a method of the invention, protein-SDS complexes are 'driven' through the extracellular matrix of decellularized tissue by subjecting the tissue to an electric field.

The above-described inventive method for electrophoretically extracting macromolecules from decellularized tissue can be implemented by using an electrophoresis system with the present invention. In one embodiment, the electrophoresis system comprises an electrophoretic apparatus in which decellularized tissue is subjected to an electric field. The apparatus itself may be any type of chamber in which tissue may be treated electrophoretically, and may adopt any shape or size. For example, the apparatus may be a tube, a square or a rectangular box, e.g., as used in conventional slab gel electrophoresis. In one embodiment, the apparatus is an electrophoretic column.

The apparatus may be made of any material, preferably electronically non-conductive material including but not limited to glass, quartz, fused silica, and polymers such as Teflon®, Delrin®, polycarbonate, polymethylmethacrylate (PMMA) or silicone. The interior of the apparatus may be coated with different material to change the surface properties for specific applications.

In various embodiments, the apparatus contains a housing, an electrode, an electrolyte chamber, a sample chamber, an electrolyte (buffer) reservoir, and any combination thereof. In one embodiment, the apparatus has a first electrolyte chamber containing a first electrode and a second electrolyte chamber containing a second electrode. For example, the apparatus can have a negative electrode (a cathode) and a positive electrode (an anode). An electrode can comprise platinum. For example, in one embodiment the positive electrode is a polypropylene finger with a platinum wire (0.5 mm diameter) coiled around it. In another embodiment, the negative electrode is a stainless steel (SS) perforated plate bent like a tube and gold plated and glued on a sintered glass filter. In a certain embodiment, the apparatus has two electrodes of opposite polarity, one of which is annular and the other of which is cylindrical.

The second electrolyte chamber can be disposed relative to the first electrolyte chamber so that the electrodes are adapted to generate an electric field in an electric field area upon application of an electric potential between the electrodes. It will be apparent to one of ordinary skin in the art of electrophoresis than the electric potential can be applied at sufficient strength and for a sufficient length of time so as to create an electric field sufficient to move a charged substance (including a macromolecule, and/or an agent such as a fixative agent, recellularization agent and/or bioactive agent) into, out of and/or through tissue that is present in the sample chamber of the apparatus. The sample chamber is disposed between the first and second electrolyte chambers and at least partially disposed in the electric field area. The apparatus includes a first electrolyte reservoir and a second electrolyte reservoir in fluid communication with the first and second electrolyte chambers, respectively. Tissue, e.g., decellularized tissue, is positioned in or on the sample chamber and placed at least partially in the electric field. Charged substances are transported between the decellularized tissue and the electrolyte and/or sample chambers. In one embodiment, tissue may be positioned in the sample chamber so as to be perpendicular to the applied electric field. The sample chamber may be configured to any shape suitable to hold a tissue of interest so that it is at least partially subjected to the electric field. Various embodiments of sample chamber, electrodes and electrolyte chamber combinations useful in the practice of the present invention will be apparent to one of ordinary skill in the art. For example, a flow chamber for treating substantially flat pieces of tissue, e.g., sheets of pericardium, or a cylinder-shaped chamber to treat cylindrically-shaped tissue can be employed.

Several electrochemical reactions take place when a potential is applied over the electrodes. At the negative electrode, $H_2$ gas is formed. At the positive electrode, $O_2$ gas and $Cl_2$ gas is formed. In certain embodiments, the cover of the electrophoretic column has an air inlet so that an inflow of air can dilute the formed gasses.

The buffer solution (rinse solution) useful in the electrophoretic apparatus and methods of the invention include rinse solutions known to the art, such as disclosed in U.S. Pat. Nos. 6,166,184 and 6,509,145; and published U.S. Patent Application Nos. 20030118981A1, 20050020506A1 and 20050266390A1. For example, aqueous solutions containing NaCl (saline) may be used. In addition, a non-phosphate saline solution can be used when rinsing. The content of the rinse solution can be between 0.1 and 1.0 weight percent saline and between about 0.025 and 0.12 weight percent sodium azide. Protease inhibitors such as EDTA, EGTA, and sodium citrate-citric acid can also be added. The bioprosthesis can be rinsed for a period of at least 600 hours, e.g., at least 200 hours, in various embodiments. The rinse solution temperature may be maintained between about 20 and 40° C. in some methods. In one embodiment of the invention, the rinse solution comprises 3 g/l NaCl and 0.5 g/l $NaN_3$ at pH 7.4.

The apparatus is suitably used at room temperature or placed in a controlled temperature environment like a cold room in order to ensure that tissue to be treated is not unduly heated prior, during or after electrophoresis. Alternatively, the apparatus may contain an interior heat sink, e.g., a cryo-unit or device such as a Peltier element, for efficiently dissipating heat from its origin. For example, the temperature of the apparatus can be controlled within the range from about −30° C. to about 30° C. through a Peltier element. In one embodiment, the temperature of the apparatus is controlled through a stainless steel cryounit. Heating may also be optionally used to maintain an optimal temperature during this processing step.

In addition, the present invention provides a system for the electrophoretic treatment of macromolecules, which system in various embodiments includes a power supply, a filter, an ion exchange column, a pump, a flow meter, a buffer (rinse solution) reservoir, or any combination thereof. The power supply can be one that provides at least 1 milliampere of electric current during electrophoresis. Such a power supply can be obtained from commercial suppliers. In one embodiment, the system has a filter to remove cellular debris and decellularization agent (e.g., SDS) from the rinse solution. In one embodiment, the filter may be a column, for example, a commercially available active carbon column. An ion exchange column is also present in some embodiments of the system, and, for example, can exchange $Cl^-$ with negatively charged ions present in the rinse solution, including SDS. For example, a commercially available amberlite $Cl^-$ column can be employed. In certain embodiments that do not employ an ion-exchange column, it may be necessary to increase the amount of buffer (rinse solution) used in order to prepare a bioprosthesis that is substantially free of SDS as compared to the amount of buffer used in embodiments of the system that do include an ion-exchange column. Using the system, electrophoretically extracted macromolecules are carried away in a stream of buffer (rinse solution) that flows over the surface of the tissue in the sample chamber of the electrophoretic apparatus. The rate of flow can be measured with a flow meter. For example, there can be zero flow of buffer, or, the flow rate of the buffer can be maintained at 0.1 to about 10 mm/s or about 0.1 L/min to about 5 L/min through the electrophoretic apparatus via a commercially available pump. In some embodiments of the system, fluid is pumped through the apparatus to impart a pulsatile force to the tissue in the sample chamber, e.g., a tissue sample can be subjected to a pulsatile flow in the physiological range for the tissue. In such embodiments, pumps capable of pulsatile flow are employed. Such pumps are commercially available. In addition, some embodiments of the system include a buffer (rinse solution) reservoir.

Because the rinse solution is regenerated using the system described herein, it is possible to use significant less chemicals and solutions as compared to currently available tissue treatment processes. Moreover, the diffusion of macromolecules from decellularized tissue can be faster as compared to conventional techniques used to rinse decellularized tissue using the electrophoretic system of the invention. Furthermore, using the system of the invention, tissue-derived bioprostheses can be prepared that are "SDS-free" and thus not cytotoxic to recipient cells when implanted, thus enhancing the ability of the bioprostheses to be recellularized by recipient cells in vivo.

In addition to or as a complement to the electrophoretic methods described herein, zone-refining, adsorption and ion-exchange techniques may be used to treat decellularized tissue in the preparation of bioprosthesis.

Figure 3:
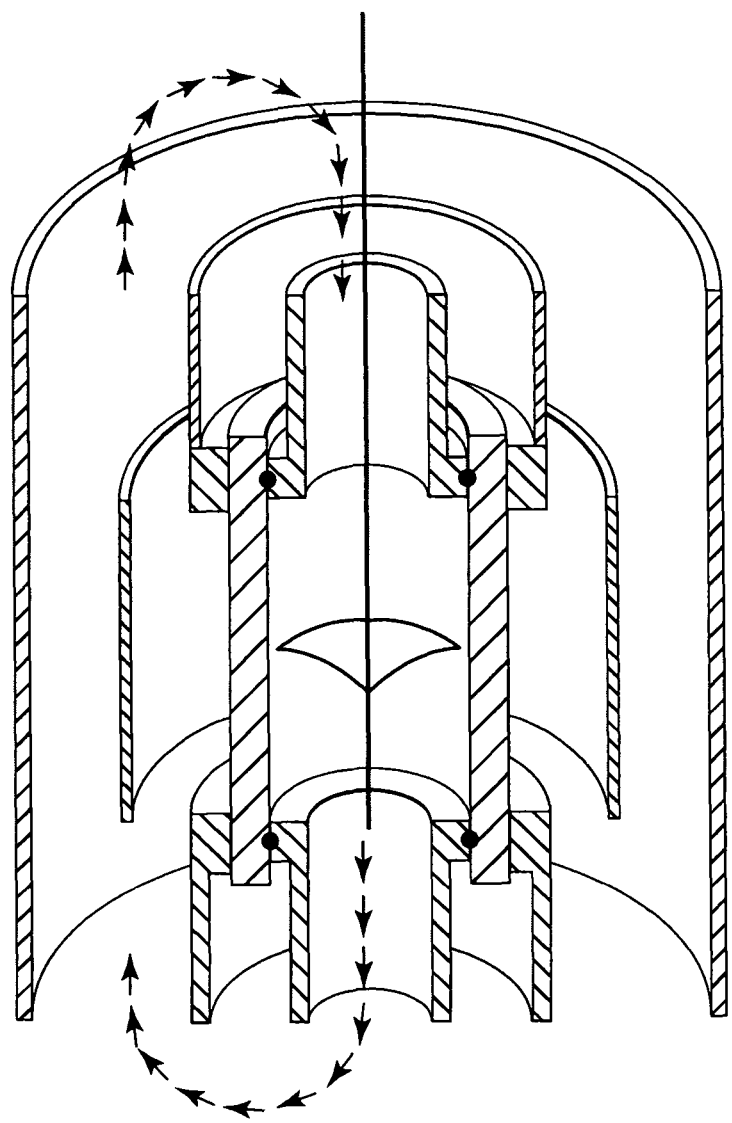
FIG. 3 shows one embodiment of an apparatus for electrophoretic treatment of tissue according to the present invention.

For example, FIG. 3 shows an apparatus for use in accordance with the present invention. FIG. 3 shows provision for movement of rinse solution past both anode and cathode during electrophoresis, either by circulating rinse solution between the electrolyte chambers (the anodic and cathodic regions) or by passing new rinse solution separately past both anodic and cathodic regions. Rinse solution circulation past the anode and cathodes may be necessary to prevent hydroxyl and hydronium ions building up at the respective electrodes as a result of continued passage of current.

Under static fluid conditions a pH gradient builds up across the tissue, rapidly preventing further passage of current, hence preventing further movement of reagents through the tissue. The circulation of fluid such as a rinse solution will prevent a pH gradient from building up thus allowing electrophoresis to continue. As discussed above, the choice of appropriate fluids will depend on the nature of the reagents to be passed through the tissue and the conditions within the tissue and should be amenable to selection by one skilled in the art of electrophoresis.

In addition, FIG. 3 shows that provision is also made for optionally applying pulsatile fluid distension along with electrophoresis to the tissue. The combination of actions can potentially enhance movement of molecules through the tissue by adding a convective movement to the interstitual fluid within the tissue that will complement electrophoretic movement of molecules through the tissue. This may be especially useful with highly organized tissue such as the aortic wall of the stentless heart valve which consists of multiple elastin lamellae with non-opposing fenestrations. In that case some combination of radial, longitudinal, and circumferential interstitial fluid motion along with radial or directed electrophoretic movement may enhance the transit rate of reagents through the tissue.

In addition, it may also be advantageous to remove pathogenic organisms by filtration or flow-through sterilization steps to enhance bioburden during electrophoretically-enhanced processing steps.

It certain embodiments of the invention, the application of an electric field enhances the speed at which charged substances migrate through tissue as well as allows for the directional treatment of tissue. For instance, the transit of charged substances through the tissue can be in one direction only. A dual process can also be envisioned where electrophoresis sweeps molecules intended for removal via decellularization from the tissue in one direction while at the same time introducing a fixative agent, or other treatment molecules such as recellularization and/or bioactive agents behind the receding decellularization front. Alternatively, treatments can be separately introduced from opposite sides of a tissue providing a bi- or multi-layer treatment process.

Provision can also be made for monitoring process parameters associated with electrophoretic treatment to maintain optimal treatment conditions and to as provide an indication of process completion.

In addition to the methods described herein, the electrophoretic apparatus and system of the present invention can be used in conjunction with known tissue treatment procedures, such as disclosed in U.S. Pat. Nos. 5,679,112; 6,177,514; 6,322,593; U.S. Patent application publication No. 2005-0119736 and International patent application Publication No. WO2002/072165. For example, the system and apparatus of the invention can be used in conjunction with the following:

i) Conventional glutaraldehyde (GTA)-fixation of tissue. Here, using the apparatus of the present invention, neutral GTA moves through the tissue via electroendosmosis (EEO). EEO occurs when the stationary tissue carries a fixed charge, usually negative. Application of a potential gradient causes hopping of the mobile opposite charge, typically sodium in a saline solution. The mobile carrier associates with water, as a result hopping of the sodium cation carries water with it and in the process moves GTA dissolved in the water along with it.

ii) Conventional GTA-fixation of tissue via movement of charged adducts of GTA through the tissue. Adducts, including blocked adducts of monomeric glutaraldehyde, such as formed by the addition of sodium bisulfite or ethylene glycol as disclosed in U.S. Pat. No. 6,177,514, can carry a negative charge. In the apparatus of the present invention, the adduct is under equilibrium with the dissociated reactants. Hence, as, for example, a charged bisulfite-GTA complex moves through the tissue, it supplies free GTA for fixation.

iii) Non-GTA fixation using reagents associated with those processes such as carbodiimide and amines.

iv) Decellularization of either fixed or unfixed tissue. Using the apparatus of the present invention, charged surfactant/protein complexes, such as those produced with detergents such as SDS, can migrate through/from tissue. The movement of a protein-SDS complex under the influence of a electric potential is the principle behind the SDS-polyacrylamide gel electrophoresis (PAGE) technique for resolving proteins in a gel. In this case, instead of a gel, the tissue, for example, valve tissue, is the stationary matrix. If the tissue carries a negative charge, then, under the principles of electroendosmosis, neutral detergent/protein complexes migrate through the tissue under the influence of an applied voltage field. Other charged molecules such as phospholipids, nucleic acids, and proteins with an inherent charge also migrate through the tissue under the influence of an applied voltage.

In addition, methods of the present invention include the use of electrophoresis for one step of the tissue processing procedure, with other steps being non-electrophoretic, as well as the use of electrophoresis for multiple steps in sequence or alternated with non-electrophoretic steps.

For example, standard rinse procedures may be employed in the methods of the present invention. In one such method, the tissue is placed in contact with the rinse solution or solutions for at least about 5 days. This rinse step is about the same length of time, or at least the same length of time, as the decellularization step in some embodiments of the invention. For example, when rinsing the tissue preparation following decellularization, the rinse step can be long enough to substantially remove decellularization agents, such as SDS, from the center of the tissue. In other embodiments of the invention, the rinse solution is replaced frequently during the process. The rinse solution can be hypotonic, and can facilitate removal of cellular components from the ECM during the duration of the rinsing process.

C. Recellularization

As discussed above, the present inventors discovered that when tissue-derived bioprostheses prepared using known techniques were implanted into recipients, the spontaneous, in vivo recellularization of the implants with host non-inflammatory cells, e.g., fibroblasts, smooth muscle cells, adipose cells, was slow when evaluated via immunohistochemical and histological methods (data not shown). One cause of the slow infiltration of non-inflammatory cells into the bioprostheses was found to be the presence of residual components of decellularization solutions, such as SDS, in the decellularized tissue of the bioprostheses. As discussed herein, the present inventors discovered that SDS can be cytotoxic to non-inflammatory cells at concentrations of about 0.006% (by weight), or about 0.5 g/L.

In addition to the methods described herein, the apparatus and system of the invention can be used to subject tissue to additional treatment steps in order to promote or enhance recellularization of a bioprosthesis once it is implanted into a recipient. For example, in certain embodiments of the invention, a bioprosthesis is contacted with a recellularization agent prior to implantation. The recellularization agent may be introduced to (and/or deposited on) the decellularized tissue using the electrophoretic system according to one embodiment of the invention.

A recellularization agent is an agent that modifies cellular interactions, such as a chemoattractant, i.e., an agent that recruits or elicits the accumulation of cells. In other embodiments of the invention, the recellularization agent is a growth factor, a cytokine, a chemokine, or any combination thereof. Growth factors are proteins that bind to receptors on the cell surface, with the primary result of activating cellular proliferation and/or differentiation. Many growth factors are quite versatile, stimulating cellular division in numerous different cell types; while others are specific to a particular cell-type. Growth factors include, but are not limited to epidermal growth factor (EGF), fibroblast growth factor (FGF), platelet derived growth factor (PDGF), transforming growth factor alpha (TGF-α), transforming growth factor beta (TGF-β), somatotropin, fibronectin, insulin-like growth factor I (IGF-I), insulin-like growth factor II, NGF, erythropoietin, and the like.

Cytokines are a unique family of growth factors. Secreted primarily from leukocytes, cytokines stimulate both the humoral and cellular immune responses, as well as the activation of phagocytic cells. Cytokines that are secreted from lymphocytes are termed lymphokines, whereas those secreted by monocytes or macrophages are termed monokines. A large family of cytokines is produced by various cells of the body. Many of the lymphokines are also known as interleukins (ILs), since they are not only secreted by leukocytes but also able to affect the cellular responses of leukocytes. Specifically, interleukins are growth factors targeted to cells of hematopoietic origin. The list of interleukins includes, but is not limited to, IL1-α, IL1-β, IL-2, IL-3, IL4, IL-5, IL-6, IL-7, IL-8, IL-9, IL-10, IL-11, IL-12 and IL-13, as well as interferons INF-α and INF-β.

Chemokines are a large superfamily of mostly small, secreted chemotactic cytokines that function in leukocyte trafficking, recruitment and activation. They also play a critical role in many normal and pathophysiological processes such as allergic responses, infectious and autoimmune diseases, angiogenesis, inflammation, tumor growth and metastasis, and hematopoietic development. Chemokines are divided into subfamilies based on conserved amino acid (aa) sequence motifs (C, CC, CXC, $CX_3C$ and others). Most family members have at least four conserved cysteine residues that form two intramolecular disulfide bonds.

In addition, in certain embodiments of the invention the bioprosthesis is treated with a biologically active (bioactive) agent prior to implantation. For example, in one embodiment of the invention, a bioactive agent, such as a therapeutic agent, is applied to the bioprosthesis of the invention by electrophoresis using the system and apparatus of the invention. Such electrophoretic application is based on the bioactive agent's inherent charge at the tissue pH and/or as a complex with a charged molecule, such as SDS. Bioactive agents useful according to the invention include virtually any substance that possesses desirable therapeutic and/or prophylactic characteristics for application to the implantation site. For example, bioactive agents include agents that mitigate calcification, e.g., as disclosed in US Pat. No. 5,679,112; agents that lead to bioburden reduction, e.g., antimicrobial agents such as antibiotics, sterilant substances such as benzyl alcohol, cetyl pyridium chloride and the like, and antiseptic agents; agents that modulate an immune response, either acute or chronic, and anti-inflammatory agents. In addition, bioactive agents useful in the present invention include anti-thrombotic agents (such as heparin, heparin sulfate, and heparin mimetics); thrombin inhibitors; antithrombogenic agents; thrombolytic agents (such as plasminogen activator, or TPA: and streptokinase); cytokines, growth factors (such as epidermal growth factor, fibroblast growth factor, platelet derived growth factor, transforming growth factor beta, somatotropin, fibronectin, insulin-like growth factor (IGF)) and other agents to modify cellular interactions, as well as agents that introduce, enhance, reduce, suppress or silence gene or messenger RNA (mRNA) expression, or protein expression. Such agents include nucleic acids, small interfering RNA (siRNA), and antisense RNA and the like.

As used herein, the term "expression" refers to the conversion of information encoded in a gene first into messenger RNA ("mRNA") and then to a protein. An "expressed gene" includes DNA transcribed into mRNA, but not translated into protein (e.g., transfer and ribosomal RNAs). The suppression or silencing of a gene is the attenuation of gene expression. Expression from a selected nucleic acid can be examined using standard methods known in the art. For example, RNA levels can be determined by Northern hybridization and in situ hybridization using the appropriate nucleic acid hybridization probes, while polypeptide levels can be determine by antibody staining and western hybridization.

The concentration of the bioactive agent in the bioprosthesis of the invention can be provided in the range of about 0.01% to about 75% by weight, or about 0.01% to about 50% by weight, based on the weight of the final bioprosthesis. In some aspects, the bioactive active agent is present in the bioprosthesis in an amount in the range of about 75% by weight or less, or in the range of about 50% by weight or less. The amount of bioactive agent in the bioprosthesis can be in the range of about 1 µg to about 10 mg, or about 100 µg to about 1000 µg, or about 300 µg to about 600 µg.

D. Sterilization Step

In certain embodiments of the invention, the bioprosthesis is sterilized using techniques known to the art. For example, the tissue scaffold and/or bioprosthesis can be contacted with a solution containing between about 0.1 and 1.0 weight percent saline, about 10 mM to 30 mM EDTA, about 0.5% to about 5.0% (by volume) Isopropyl alcohol, and about 0.1% to 0.25% (by weight) cetylpyridinium chloride (CPC). The bioprosthesis can contact the sterilization solution for 1 hour to 3 hours in some embodiments, and about 3 hours in one embodiment. In certain embodiments of the invention, a "cold chemical treatment" is employed to sterilize the tissue scaffold and/or bioprosthesis, as described in U.S. Patent application publication No. 20050266390.

E. Storage

In certain embodiments of the invention, harvested tissue is stored for later processing. Different methods may be used to preserve the tissue during storage including cryopreservation and drying according to a variety of protocols. In addition, the tissue-derived bioprosthesis may be stored or alternatively further processed as described herein or according to known tissue engineering methodology, or implanted into the body of a recipient.

After sterilization, the bioprosthesis can be packaged in storage solution. Techniques for storage are known to the art. For example, a storage solution with about 0.1% to about 1.0% (by weight) saline, about 10 mM to about 30 mM EDTA, about 5 mM to about 20 mM HEPES at pH 7.4, and about 0.01% to 0.1% (by weight) sodium azide may be used. The tissue may be stored at temperatures between about 0° C. to 40° C. until use.

The invention will be further described by, but is not limited to, the following example.

EXAMPLE 1

Electrophoretic Column and System

Summary

An electrophoretic column and system was developed and used to rinse decellularized heart valves. Using this column and system, SDS was continuously removed from the rinse solution, thereby creating a concentration gradient enabling rapid diffusion of SDS from the tissue as compared to conventional rinse procedures. Furthermore, an electric field within the electrophoretic column, applied perpendicularly to the tissue, drove SDS out of the tissue. A numerical model of the inventive processes was created and used to simulate the uptake in and release of SDS from tissue. The rinse capacity of the electrophoretic column was influenced by the applied inflow velocity of the rinse solution, the applied potential over the electrodes, and by the conductivity of the rinse solution.

Experiments on the uptake in and release of SDS from tissue were carried out. Tissue samples were enzymatically digested and measured with UVvis. Histology was performed on the tissue to determine the influence of the applied potential on the structural elements of the extra cellular matrix (ECM) of the tissue.

Conventional rinse procedures take approximately 1140 hours. In contrast, decellularized tissue can be effectively rinsed with the electrophoretic column in approximately 515 hours, which is 55% faster than the standard rinse procedure. Moreover, it was discovered that decellularization time could be reduced to about 50 hours, which is 30% of the decellularization time in currently used tissue treatment procedures. The reduced decellularization time results in a lower initial amount of SDS within the tissue, which tissue can then be rinsed almost 20% faster than the decellularized tissue prepared using conventional methods. Furthermore, the histological evaluation of the tissue rinsed with the electrophoretic column showed that structural elements of the ECM are not affected by the applied potential.

Materials and Methods

1. Decellularization of Porcine Aortic Valves

Fresh porcine aortic valves were dissected, freed from adherent fat and most of the myocardium, and washed in 3 g/l NaCl, 0.5 g/l NaN$_3$, 20 mM ethylenediaminetetraacetic acid disodium salt dehydrate (EDTA) and 1 ml/l Protease Inhibitor (PI) cocktail (Sigma P2714) for 24 hours at room temperature. The fresh valves were then transferred to a decellularization solution containing 5 g/l SDS, 5 g/l Triton X-100, 3 g/l NaCl and 0.5 g/l NaN$_3$ at pH 7.4 and processed in roller bottles. Each roller bottle contained 4 valves and approximately 2 liters of decellularization solution and was continuously rolled. The solution was replaced once each 24 hours. Processing time depends on the valve size, but was minimally 7 days (168 hours) at room temperature. At several time points, samples (diameter approximately 4.6 mm) of the aortic wall of three random valves (n=3) were punched out of the aortic wall. The samples were dabbed dry with tissue paper, weighed (referred to as wet weight) and stored at −30° C. The completely frozen samples were freeze-dried, and afterwards the dry weight was determined. These samples were used to determine the uptake of SDS in tissue over time.

The decellularized valves were then placed in a roller bottle, with approximately 0.5 l rinse solution per valve. The rinse solution contained 3 g/l NaCl and 0.5 g/l NaN$_3$ at pH 7.4. The decellularized valves were rinsed at room temperature for at least 7 days (168 hours), depending on valve size, and the rinse solution was changed three times a day.

To determine the release of SDS from tissue, at several time points three valves (n=3) were removed from the roller bottles and the tissue was dabbed dry with tissue paper. Samples (diameter approximately 4.6 mm) were punched out of the aortic wall. The wet weight of the samples was determined and the samples were stored at −30° C. The completely frozen samples were freeze-dried and afterwards the dry weight was determined.

2. Sodium Dodecyl Sulphate (SDS)

SDS is retained within tissue when used as a decellularization agent. Wilson et al., *Ann. Thorac. Surg.,* 60:S353-8 (1995); Kasimir et al., *Int. J. Artif. Organs,* 26:421-7 (2003); and Rieder et al., *J. Thorac. Cardiovasc. Surg.,* 127:399-405 (2004). The negatively charged detergent SDS, an ester of sulfuric acid and dodecyl alcohol, binds effectively to proteins via its hydrophobic domain, leaving its hydrophilic region exposed and generating an increased negative charge (Korossis et al., *J. Heart Valve Dis.,* 11:463-71 (2002)). This charge leads both to swelling and decreased stability of the tissue. Elastin retains increasing amounts of SDS in parallel with the increase in the concentration of SDS. Moreover, the capacity of elastin to retain SDS is increased by NaCl containing medium (Kawazoye et al., *J. Biochem.* (Tokyo), 117: 1254-60 (1995)). The rate of loss of SDS from elastin during repeated washings is also influenced by NaCl. SDS is more effectively removed by washing with NaCl-free medium.

Hirsch measured sodium dodecyl [$^{35}$S]-sulphate diffusivity across gluteraldehyde cross-linked porcine aortic valve leaflets using two chamber diffusion cells at 37° C. under constant shaking (Hirsch, *J. Biomed. Mater. Res.,* 27:1477-84 (1993)). The maximum uptake of SDS in leaflets in 1%, 0.5% and 0.1% (w/v) solutions of SDS was determined as well as the partition coefficient $K_p$ of leaflets was also determined.

3. Enzymatic Degradation of Tissue

To measure the SDS content in tissue, it must be digested. However, high concentration HCl and NaOH digestion protocols cannot be used because SDS breaks down at low and high values of pH. Moreover, enzymatic digestion with collagenase did not give satisfactory results. Thus, tissue was digested using protease from *Streptomyces griseus* (Sigma, P5147). In particular, at least 3 units/ml protease was used in 9 g/l NaCl, 10 mM HEPES hemisodium salt (Sigma, H7637), 0.6 g/l CaCl22H20 (Sigma, C5080) and 7.5 g/l (0.1 M) glycine (Sigma, G7126) at pH 7.4. To each freeze-dried sample of the heart valves, 3 to 5 ml of this solution was added and incubated for at least 24 hours (depending on sample size) at 37° C. under continuous shaking.

4. SDS Measurement

The positively charged dye acridine orange (AO) was added to the solution containing SDS to form AO-SDS complexes. Toluene was added to this solution to extract the SDS-AO complex. The AO-SDS complex in the toluene phase had an absorption peak of 499 nm and was therefore measured and evaluated with UV-vis using a modified method of Sokoloff et al. (Sokoloff et al., *Anal. Biochem.,* 118:138-41 (1981)). In particular, the pH of the protease solution was changed to approximately pH 2 by adding HCl to prevent protein-AO complexes from being extracted into the toluene phase. The lowered pH caused the protein and protein fragments to precipitate out of solution, and therefore no complexes with AO were formed. UV-vis spectrum was measured with an Agilent 8453 UV-visible spectrophotometer (Agilent Technologies, Germany).

Samples with different concentrations of SDS were created from a stock solution of 0.02432% (w/w) SDS in protease buffer. A 1% AO (Aldrich 15,855-0) 0.05 M HCl solution was created. From each sample containing SDS, three samples (n=3) of 100 µl were taken and to each 100 µl of AO solution was added. Subsequently 3 ml of toluene was added and the whole was shaken vigorously. The test tubes were centrifuged at 2000 rpm for 5 minutes. A calibration curve was determined by measuring the absorbance of the toluene phase at 499 nm. Toluene served as reference and protease buffer without SDS was measured for background correction (n=3).

5. The Electrophoretic System

An electrophoretic system, which employed an electrophoretic apparatus, was developed to improve upon standard rinse procedures used in the treatment of decellularized porcine heart valve tissue. The system had an electrophoretic column (with an air inlet), an Amberlite Cl column, an active carbon column, a pump (Biomedicus pump, model 540E, serial 3033, Medtronic, Minneapolis, Minn., USA), a power supply (model 2197, serial 9705, LKB Bromma, Sweden), a flow meter, and a buffer reservoir. The system was a closed system having a volume of approximately three liters of fluid.

6. Concentration Gradient

To ensure the fastest possible diffusion of SDS out of the tissue, the concentration gradient was maximized by keeping the concentration of SDS in the fluid low. The electrophoretic system was filled with three liters of a 3 g/l NaCl solution. To maintain the concentration of SDS in the fluid near zero, the fluid in the system was transported through two columns. One column was packed with approximately 100 g active carbon (Aldrich, 32,942-8) and the other with approximately 100 g Amberlite IRA-400 Cl- (Fluka, 06431).

7. Electric Field

The positive electrode of the electrophoretic column was a polypropylene finger with a platinum wire (0.5 mm diameter) coiled around it. The negative electrode was a stainless steel (SS) perforated plate bent like a tube and gold plated and glued on a sintered glass filter. A potential was applied over these electrodes with a power supply, which created an electrical field between the electrodes perpendicular to the tissue. This electric field induced two different forces within the tissue: attraction and repulsion of components based on their charge, an electro motive force (EMF) and an electro osmotic flow (EOF). The EOF was based upon the fact that the tissue was slightly negatively charged, thus attracting positive components of the tissue fluid. The positively charged tissue fluid layer was attracted toward the negatively charged electrode, inducing a plug flow of tissue fluid towards the negative electrode. This plug flow drags everything within the tissue fluid, both charged and uncharged components. Even negatively charged components, like SDS, can be moved towards the negative electrode if the electric field is strong enough to generate an EOF bigger than the EMF of SDS. The total amount of fluid may decrease over time because of the reactions at the electrodes, thus it may be necessary to introduce additional fluid into the system over time.

8. Numerical Model

A numerical model of the electrophoretic column was developed. The finite element package SEPRAN (SEPRA, Leidschendam, the Netherlands) was used. Using the numerical model, the diffusion of SDS into tissue was simulated by setting the initial $[SDS]_{tissue}$ to 0 g/l and the [SDS]fluid to 5 g/l. In currently used decellularization processes, the solution containing SDS is changed once every 24 hours for at least 168 hours. This changing of solutions was simulated by applying an inflow with an essential boundary condition at this inflow area where the concentration of SDS was set to $[SDS]_{fluid}$. With a total volume of approximately three liters, the inflow velocity $v_m$ was calculated to be approximately $7 \cdot 10^{-3}$ mm/s. By evaluating the concentration profile over the tissue thickness, the time needed for SDS to migrate to the center of the tissue was predicted. A reduced decellularization time was estimated by combining the toxic concentration of SDS for cells (0.5 g/l) with the migration time to the centre of the tissue (thickness of 2 mm).

The numerical model was also used to simulate a standard rinse procedure, in particular, rinsing heart valves in a SDS free solution that is changed at least 3 times a day. To simulate this changing of solutions, the inflow velocity $v_m$ was calculated to be approximately $2 \cdot 10^{-2}$ mm/s. The initial $[SDS]_{tissue}$ was set to concentration distribution at the end of the decellularization process calculated with the numerical model and the $[SDS]_{fluid}$ was set to 0 g/l. An essential boundary condition was introduced at the inflow area; the concentration of SDS was set to zero. The results were compared with the experimental data. The concentration distribution at which the toxic concentration of SDS for cells was reached in the middle of the tissue was used as input for an optimized release simulation. The results were compared with the normal uptake and release and the time gain was calculated.

In addition, the numerical model was used to simulate the rinse procedure using the electrophoretic column. The electric field produced when potential is applied over the column's electrodes induces a velocity field within the tissue. The applied potential over the electrodes was 2 V and the applied flow was 0.5 l/min ($v_m$=1.67 mm/s). The initial $[SDS]_{tissue}$ was set to concentration distribution at the end of the decellularization process calculated with the numerical model and the $[SDS]_{fluid}$ was set to 0 g/l. An essential boundary condition was introduced at the inflow area; the concentration of SDS was set to zero. The inflow velocity $v_m$ was varied (0, 0.33, 1.67 and 6.6 mm/s) in simulations without and with an applied potential (20V) to give insight in the influence of the applied flow rate the solution of the numerical model. Furthermore the applied potential was varied (0, 2, 4, 8, 20 and 40 V) to give insight in the effect on the rinse procedure. Finally, several simulations were done where the conductivity of the fluid was varied. The conductivity of the fluid is dependent of the concentration of NaCl as shown in Table 1 (below).

TABLE 1

| [NaCl] (g/l) | Conductivity (S/mm) |
|---|---|
| 1 | $1.8 \cdot 10^{-4}$ |
| 2 | $3.7 \cdot 10^{-4}$ |
| 3 | $5.5 \cdot 10^{-4}$ |
| 6 | $1.11 \cdot 10^{-4}$ |
| 9 | $1.66 \cdot 10^{-3}$ |

The concentration distribution at which the toxic concentration of SDS for cells was reached in the middle of the tissue was used as input for an optimized release simulation with an applied potential of 2 V. The results were compared with the uptake and rinse with the electrophoretic column. The time gain was calculated.

The numerical model was used to determine an optimal uptake and rinse procedure for the bioprosthetic material. The uptake of SDS in tissue was evaluated with a potential of 20 V applied over the electrodes for approximately 1.1 hours. The initial $[SDS]_{tissue}$ was set to 0 g/l and the $[SDS]_{fluid}$ to 5 g/l. An essential boundary condition was applied at the inflow area where the concentration of SDS was set to $[SDS]_{fluid}$. Subsequently the tissue was rinsed with a potential of 20 V applied over the electrodes for 55.6 hours. The initial $[SDS]_{tissue}$ was set to concentration distribution at the end of the optimized uptake process calculated with the numerical model. The $[SDS]_{fluid}$ was set to 0 g/l and an essential boundary condition was introduced at the inflow area; the concentration of SDS was set to zero. The applied flow rate during the uptake and release simulation was 0.5 l/min ($v_m$=1.67 mm/s).

9. Uptake of SDS in Tissue

Porcine hearts were obtained from a local slaughterhouse. Warm ischemic time was less than 2 hours. The aortic valves were dissected and freed from adherent fat and most of the myocardium and immediately transferred to a 9 g/l NaCl solution (Merck, 106404). Subsequently, the valves were washed in a 9 g/l NaCl and 0.5 g/l NaN$_3$ solution (Merck, 106688) for 22 hours. To get rid of residual blood the valves were finally washed with a 3 g/l NaCl, 0.5 g/l NaN$_3$ and 20 mM EDTA pH 7.4, solution (Sigma, E4884), for 21.5 hours. All steps conducted at room temperature under continuous shaking with 0.5 l solution per valve. The pH was measured with a Philips PW9422 pH-meter (Philips, the Netherlands). The valves were stored at 4° C. in a 9 g/l NaCl, 0.5 g/l NaN$_3$ and 20 mM HEPES hemisodium salt solution (Fluka, 54467) until further processing.

Subsequently, the valves were immersed in a 5 g/l SDS (Fluka, 71729), 5 g/l Triton X-100 (Aldrich, 23,472-9), 3 g/l NaCl and 0.5 g/l NaN$_3$ solution at pH 7.4 for approximately 340 hours at room temperature under continuous shaking, with 0.25 l solution per valve. (Normally, 0.5 l solution per valve is used, but this experiment contained valves without a full aortic root.) The solution was changed every 24 hours. At certain time points, 6 random valves (n=6) were removed from the solution and dabbed dry with tissue paper. With a 6 mm diameter punch, samples of the aortic wall of the valves were taken and stored at −30° C. The completely frozen samples were subsequently freeze-dried and afterwards the weight of these samples was determined. The samples were enzymatically digested and used to determine the uptake of SDS in tissue over time. The data were used to fit the numerical model and the partition and diffusion coefficients were determined.

10. Rinsing with the Electrophoretic Column

A sample with a diameter of approximately 4.6 mm was punched out of the aortic wall and a decellularized aortic heart valve. The sample was weighed and stored at −30° C. The valve was inserted into the electrophoretic column over the central electrode and a constant flow rate of 0.5 l/min was applied. The power supply was set to a constant current of 15 mA, with the central electrode as positive electrode and the outer electrode as negative electrode. The applied potential at this current was approximately 2 V. At several time points the power supply was shut down and the valve was taken out of the electrophoretic column and dabbed dry with tissue paper. A sample was punched out of the aortic wall (diameter approximately 4.6 mm) and the wet weight of the sample was determined, the valve was replaced in the column and the initial flow rate and current were applied. The sample was stored at −30° C. and afterwards freeze-dried. After freeze-drying, the dry weight of the samples was determined and the samples were enzymatically digested and used to determine the release of SDS from tissue over time. The results were compared with data obtained from the standard rinse procedure to determine the possible performance gain. The data were used to fit the numerical model and the total mobility of SDS was determined.

11. Histology

Fresh, decellularized and standard rinsed porcine aortic heart valve wall tissue was stained with hematoxiline-eosine (HE) for histological evaluation at a magnification of 5×. Further histology was performed on tissue rinsed with the electrophoretic column, using HE and Movat's Pentachrome (Movat) staining (at a magnification of 10×). All samples were evaluated for the presence of cells, and/or cell remnants, as well as for the general structure of the extra cellular matrix (ECM).

Results

1. UV-vis

The spectra of the toluene phase of different concentrations of SDS in protease buffer were measured with UV-vis at 499 nm. The absorbance of protease buffer without SDS was 0.0142, with a standard deviation of 0.0006, and was used for background correction. The data were plotted and a calibration curve determined (data not shown). A linear fit ($R^2$=0.9944) through the data points resulted in the following equation, which was used to determine the amount of SDS in the tissue samples:

$$[SDS]=(19.84)(Absorbance)$$

2. Uptake of SDS in Tissue

Decellularization of porcine aortic valves resulted in an uptake of SDS in the tissue. The amount of SDS increased with time. A maximum mean $[SDS]_{tissue}$ of 45 g/l was measured after almost 350 hours of decellularization. At the end of 168 hours of decellularization, the mean $[SDS]_{tissue}$ was roughly 25 g/l.

3. Release of SDS from Tissue

The mean $[SDS]_{tissue}$ at the start of both the standard rinse procedure and rinsing with the electrophoretic column was approximately 25 g/l. The initial release of SDS from tissue in the standard rinse procedure was faster than rinsing with the electrophoretic column. However, it takes over 500 hours of standard rinsing (n=3) before the mean $[SDS]_{tissue}$ was below 5 g/l in comparison with the electrophoretic column (n=1), where this level was reached just before 200 hours of rinsing. This is a time performance gain of approximately 60%. After approximately 190 hours of standard rinsing the mean $[SDS]_{tissue}$ was 7.5 g/l and 3.7 g/l for rinsing with the electrophoretic column.

According to the numerical model, the toxic concentration of SDS for cells (0.5 g/l) is reached after approximately 1140 hours of rinsing. With a decellularization time of 168 hours, the total processing time to produce a 'SDS-free' valve is approximately 1305 hours, or roughly 54.5 days.

The toxic concentration of SDS for cells (0.5 g/l) was reached after approximately 520 hours of rinsing. This is a time gain of approximately 620 hours compared with the standard rinse procedure. The time performance gain thereby is approximately 55%. The total processing time for a 'SDS-free' heart valve substitute thereby is approximately 680 hours, which is around 28.5 days.

A comparison was made between the experimental and numerical results. The MAE for the standard rinse procedure was calculated to be 1.63 g/l. In the standard rinse procedure the mean, $[SDS]_{experiment}$ was 9.7 g/l, so the RE was 16.78%. For the electrophoretic column, the MAE was 1.61 g/l and the mean $[SDS]_{experiment}$ was 15.2 g/l and so the RE was 10.56%.

4. Decellularization Time

A plot of the concentration of SDS over the cross section of the tissue (data not shown) showed that at approximately 50 hours of decellularization, the concentration of SDS at the middle of the tissue has reached the toxic concentration of SDS for cells. The mean $[SDS]_{tissue}$ at this time was approximately 15 g/l.

5. Release of SDS

The concentration profile after 50 hours of decellularization (not shown) was used as an input for an optimized release simulation. The release of SDS from tissue over time for both the standard and the optimized rinse was plotted (not shown). The mean $[SDS]_{tissue}$ at the start of the optimized rinse procedure was roughly 15 g/l, which was 10 g/l less than the standard rinse procedure. It would take approximately 900 hours of rinsing before the toxic concentration of SDS for cells was reached, which is 240 hours faster than the standard rinse procedure for a time performance gain of 21%. A 'SDS-free' heart valve can be produced in approximately 950 hours (39.5 days) with this procedure.

The concentration profile after 50 hours of decellularization was also used as an input for a release simulation with an applied potential over the electrodes of 2 V. In this simulation it takes approximately 425 hours of rinsing before the toxic concentration of SDS for cells is reached. This is roughly 90 hours faster than rinsing with the electrophoretic column without an optimal uptake of SDS. This is a time performance gain of almost 18%. The total processing time for a 'SDS-free' heart valve is therefore approximately 475 hours (20 days).

6. Factors Influencing the Release of SDS from Tissue a. Effect of the applied flow The flow rate of the electrophoretic system can be adjusted, resulting in a uniform inflow velocity $v_m$. Several runs with different inflow velocities were carried out without an applied potential. The data were plotted against rinse time (not shown). The solution without any flow (v=0 mm/s) showed a much slower release of SDS compared with the solutions with an applied flow. Solutions with different applied inflow velocity show comparable release patterns for SDS from tissue over time.

The effect of the inflow velocity was also studied with an applied potential of 20 V. The higher the inflow velocity, the faster the SDS was released from the tissue (data not shown). The toxic concentration of SDS for cells was reached after different rinsing times. The results are shown in Table 2. If the inflow velocity is raised from 0.33 to 6.6 mm/s, the rinse time can be shortened by 3.1 hours, for a time performance gain of 4.6%. For the percent difference (%Δ) calculations, the value at the inflow velocity of 6.6 mm/s was used as reference.

TABLE 2

| Inflow velocity (mm/s) | Rinse time (hours) | Percent difference (%) |
|---|---|---|
| 0.33 | 67 | 4.74 |
| 1.67 | 64.8 | 1.4 |
| 3.3 | 64.2 | 0.47 |
| 6.6 | 63.9 | 0 | b. Effect of the applied potential

Varying the applied potential influences the release of SDS from tissue. The higher the applied potential, the faster SDS was released from the tissue (data not shown). A convergence of the solution for the increasing applied potential was visible. The time required to reduce the mean $[SDS]_{tissue}$ under influence of an applied potential to the toxic concentration of SDS for cells is depicted in Table 3. The rinse time can be shorted approximately 1000 hours if a potential of 20 V is applied, for a time performance gain of 94%. If the potential is doubled to 40 V, the rinse time can be shortened by 31 hours, a time performance gain of 96.9%. When plotted, the applied potential showed a linear relationship with the reciprocal values of the required rinse time (y=1387x−0.9516; $R_2$=0.9996).

TABLE 3

| Applied potential (V) | Rinse time (hours) | Time performance gain (%) |
|---|---|---|
| 0 | 1080 | 0 |
| 2 | 516 | 52.2 |
| 4 | 296 | 72.6 |
| 8 | 155.5 | 85.6 |
| 20 | 65 | 94.0 |
| 40 | 34 | 96.9 |

The potential field calculated with the numerical model, with 2 V applied over the electrodes was plotted. The highest potential was found at the central electrode. The potential was decreasing from the central positive electrode toward the negative electrode. The potential distribution in the tissue was not uniform. At the bottom and top of the tissue, the potential was slightly lower than in the middle of the tissue.

c. Effect of the conductivity of the fluid

When the conductivity of the rinse solution was low, SDS released slowly from the tissue (data not shown). When the conductivity was raised, SDS was released more quickly. Table 4 shows the effect of the concentration of NaCl (i.e., the conductivity of the fluid), on the mean $[SDS]_{tissue}$ after 45 hours of rinse time. Currently used rinse procedures use, for example, a solution having 3 g/l NaCl. The result of this simulation is used as reference (100%) to calculate the difference between the mean $[SDS]_{tissue}$ of the simulations. According to the numerical model, increasing the concentration of NaCl from 3 to 9 g/l will lower the mean $[SDS]_{tissue}$ by 95% after 45 hours of rinsing.

TABLE 4

| [NaCl] (g/l) | [SDS] (g/) | [SDS]tissue different (%) |
|---|---|---|
| 1 | 8.90 | 383.6 |
| 2 | 4.71 | 203.0 |
| 3 | 2.32 | 100.0 |
| 6 | 0.37 | 15.9 |
| 9 | 0.12 | 5.2 | d. Uptake and release of SDS with electric field

After decellularizing the tissue for 1.1 hours, the mean $[SDS]_{tissue}$ was approximately 3 g/l. This concentration distribution was used for in a release simulation. Using the electrophoretic column, the release of SDS from tissue over time was plotted (data not shown). The plot showed a quick drop in mean $[SDS]_{tissue}$. Then, the plot showed a plateau level of mean $[SDS]_{tissue}$ of around 1.4 g/l from 8 to 20 hours of rinsing. The toxic concentration of SDS for cells was reached after 40 hours of rinsing. The total processing time for preparing a "SDS-free" decellularized heart valve comes to approximately 41 hours.

The concentration of SDS (g/L) in the middle of the tissue was plotted against time (the inner radius of the heart valve was 15 mm; the outer radius of the heart valve was 17 mm; data not shown). Initially, the concentration was found to be below the toxic concentration of SDS for cells. As rinse time increased, SDS was transported through the tissue towards the negative electrode of the electrophoretic column. The toxic concentration of SDS for cells was reached over the whole cross section in time. At the end of the simulation time, the mean $[SDS]_{tissue}$ was below the toxic concentration of SDS for cells.

e. Histology

Cross-sections of porcine aortic heart valve wall samples were stained with hematoxylin-eosin (HE) and photographed at 5× magnification (data not shown). In the HE-stained section of the fresh porcine aortic heart valve wall sample, cell nuclei were clearly visible just before entering the decellularization process. At the end of the decellularization process, before entering the standard rinse process, some cells and/or cell remnants were visible. The structural elements of the extra cellular matrix (ECM), elastin and collagen, were comparable to that of fresh valve ECM. The standard rinsed decellularized valve sample showed no cells or cell remnants. The structural elements of the ECM were comparable to the ECM of the fresh valve, but more open spaces were visible. There was no indication of ECM damage caused by the decellularization process.

Decellularized porcine aortic heart valve wall samples were rinsed with the electrophoretic column in combination with an electric field. HE-sections and Movat stained sections were photographed at 10× magnification (data not shown). Histological evaluation revealed no visible cells in the wall or leaflet in both the HE and the Movat stained sections. The ECM of the heart valve wall stained with HE was comparable to that of the standard rinsed valve.

Discussion

Tissue is conventionally decellularized with SDS when preparing bioprostheses such as heart valve substitutes. However, the literature reports that SDS is retained in tissue even after extensive rinsing. See, for example, Wilson et al., *Ann. Thorac. Sure.*, 60:S353-8 (1995); Kasimir et al., *Int. J. Artif. Organs*, 26:421-7 (2003); and Rieder et al., *J. Thorac. Cardiovasc. Surg.*, 127:399-405 (2004). Using the methods and apparatus of the present invention, SDS is rinsed out of the tissue more effectively than the currently used procedures.

The SDS content of tissue samples was measured with an acridine orange (AO) solution, and according to the calibration curve, can be measured as low as 0.25 µg/100 µl sample.

Simulations on the uptake of SDS in tissue were fitted on experimental results. From this fit the partition coefficient, diffusion coefficients and total mobility of SDS were determined. Experimental data on the uptake of SDS in tissue was acquired at two different locations at different moments in time match. Using standard rinsing procedures, the mean $[SDS]_{tissue}$ was found to be about 5 g/l after 500 hours. The same concentration was reached in less than 200 hours using the apparatus of the present invention, for a time performance gain of more than 60%.

The mean $[SDS]_{tissue}$ rinsed with the apparatus of the present invention was 50% less than the $[SDS]_{tissue}$ rinsed using a standard rinse procedure after 190 hours of rinsing. According to the numerical model described herein, it would take approximately 1140 hours before the mean $[SDS]_{tissue}$ reached levels below the toxic concentration of SDS for cells using standard tissue treatment methods, for a total processing time to create a "SDS-free" of approximately 1305 hours. The release of SDS from tissue rinsed in the electrophoretic column was simulated, and found to take 520 hours before the levels below that of the toxic concentration of SDS for cells was reached, for a time performance gain of almost 55%. The total processing time to create a "SDS-free" substitute was 680 hours, for a total time performance gain of about 48%.

In standard rinse procedures, SDS diffuses out of the tissue. The apparatus of the present invention rinses tissue under influence of an electric field, which induces a movement of SDS within the tissue. With an applied electric field, a part of the SDS in the tissue is transported through the tissue instead of diffusing out of the tissue.

Because SDS is difficult to remove from tissue, the first step to reduce the rinse time was to reduce the initial amount of SDS in the tissue. A reduced decellularization time was determined by setting the minimum amount of SDS in the middle of the tissue to the toxic concentration of SDS for cells. The reduced decellularization time was determined to be 50 hours, which is 70% less time than the current decellularization time (168 hours). The mean $[SDS]_{tissue}$ at the end of the normal decellularization was 25 g/l, whereas the mean $[SDS]_{tissue}$ after the reduced decellularization time was 15 g/l, which is 40% less SDS. The concentration distribution within the tissue after 50 hours of decellularization was used as input for the numerical model in an optimized release simulation. The time required to get the mean $[SDS]_{tissue}$ below the toxic concentration of SDS for cells was 900 hours, a time performance gain of 21% in comparison with the standard uptake and release. The same simulation was done with an electric field driving SDS out of the tissue. After 425 hours, the mean $[SDS]_{tissue}$ was below the toxic level, i.e., 90 hours faster using the electrophoretic column than the normal rinse method. For tissue thicker than 2 mm, longer decellularization times may be needed.

The effect of the inflow velocity of a rinse solution using the numerical model is clear. When SDS is released from tissue, a concentration layer around the tissue is formed. If inflow is not applied, SDS simply diffuses out of the tissue into the surrounding fluid and builds up if not removed from the solution, resulting in even slower release of SDS from tissue. In the case of an applied inflow, SDS in the fluid is transported away from the tissue and removed from the fluid. The higher the inflow velocity, the thinner the concentration boundary layer and the faster the SDS can diffuse out of the tissue. In case of an applied potential, SDS is released from the tissue more quickly, and the inflow velocity becomes more important. The relative difference between the maximal inflow velocity of 6.6 and 1.67 mm/s is 1.4%. SDS can be removed from the solution in the active carbon and amberlite columns. If the velocity within the column is too high, the removal of SDS might not be complete. Therefore, an inflow velocity of 1.67 mm/s (0.5 l/min) was used.

Using the electrophoretic column, a potential was applied over the electrodes to generate an electric field between the electrodes that was perpendicular to the tissue. The current was set to a constant value of 15 mA and the applied potential was 2 V. The potential was varied in several simulations. The higher the potential, the higher the electric field between the electrodes and thus the faster SDS can be rinsed out of the tissue. The relationship between applied potential and the reciprocal value of the required rinse time was linear. If the applied potential is increased from 20 to 40 V, the rinse time can be shortened by 3%. With a potential of 2 V and a current of 15 mA, the mean resistance of the medium between the electrodes was 133Ω. If the mean resistance of the medium between the electrodes is considered constant, the current at a potential of 20 V would be 150 mA. Higher current results in more gas and heat production. In embodiments of the present invention, the solution entering apparatus or the whole apparatus itself is cooled.

Histological evaluation of aortic wall acquired from the two different rinse procedures showed that there were no cells or cell remnants visible. The structural elements of the ECM after rinsing with the electrophoretic column look the same as in fresh tissue.

Using an applied potential of 2 V in the electrophoretic system, the time required to rinse decellularized tissue was reduced by 620 hours, for a performance gain of 55%. To further reduce rinse time, the decellularization time was also reduced to 50 hours. If the concentration distribution in tissue at the reduced decellularization time is taken as starting point of the rinsing, the calculated required rinse time is 425 hours. This is a time reduction of 715 hours or almost 63%. Furthermore, the histological evaluation of the tissue rinsed with the electrophoretic column showed that the structural elements of the ECM are not affected by the applied potential.

The foregoing description is considered as illustrative only of the principles of the invention. Further, since numerous modifications and changes will readily occur to those skilled in the art, it is not desired to limit the invention to the exact construction and process shown as described above. Accordingly, all suitable modifications and equivalents may be resorted to falling within the scope of the invention.

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. A method for preparing a tissue-derived bioprosthesis, comprising:
    contacting tissue treated with a decellularization solution comprising a decellularization agent with a rinse solution in an electrophoretic field; and
    electrophoretically extracting the decellularization agent from the tissue to provide tissue substantially free of the decellularization agent, wherein a level of the decellularization agent in the tissue following the step of electrophoretically extracting the decellularization agent is sufficiently low such that the tissue may readily recellularize in vivo.

2. The method of claim 1, wherein the tissue treated with the decellularization solution is contacted with the decellularization solution for up to about 170 hours.

3. The method of claim 1, wherein the tissue is mammalian tissue.

4. The method of claim 3, wherein the mammalian tissue is aortic tissue, pericardial tissue, venous tissue, arterial tissue, a component thereof or any combination thereof.

5. The method of claim 4, wherein the aortic tissue comprises collagen, elastin, hyaluronic acid, or any combination thereof.

6. The method of claim 3, wherein the mammalian tissue is human, porcine, bovine, marsupial, ovine, or canine tissue.

7. The method of claim 6, wherein the mammalian tissue is porcine tissue or bovine tissue.

8. The method of claim 1, wherein the tissue comprises fresh tissue, cadaveric tissue, fixed tissue or unfixed tissue.

9. The method of claim 1, wherein the decellularization agent comprises a negatively charged molecule.

10. The method of claim 1, wherein the decellularization agent comprises an ionic detergent.

11. The method of claim 10, wherein the ionic detergent is an anionic detergent.

12. The method of claim 11, wherein the anionic detergent is sodium dodecyl sulphate or a derivative thereof.

13. The method of claim 12, wherein the bioprosthesis is substantially free of sodium dodecyl sulphate.

14. The method of claim 1, wherein the step of contacting the tissue with a rinse solution in an electrophoretic field includes subjecting the tissue to the electrophoretic field for less than 600 hours.

15. The method of claim 1, further comprising washing the tissue to remove tissue debris, blood, fluid, fat, or any combination thereof.

16. The method of claim 1, wherein the decellularization agent associates with a macromolecule present in the tissue to provide a complex.

17. The method of claim 16, wherein the macromolecule is selected from the group consisting of a protein and a nucleic acid.

18. The method of claim 16, wherein the step of electrophoretically extracting the decellularization agent from the tissue further provides tissue substantially free of the complex.

19. A method for preparing a tissue-derived bioprosthesis, comprising:
    contacting tissue treated with a decellularization solution comprising a decellularization agent with a rinse solution in an electrophoretic field;
    electrophoretically extracting the decellularization agent from the tissue to provide tissue substantially free of the decellularization agent; and
    electrophoretically introducing a recellularization agent to the decellularized tissue.

* * * * *